United States Patent [19]
Takahashi et al.

[11] Patent Number: 4,925,969
[45] Date of Patent: May 15, 1990

[54] PROCESS FOR PREPARING ETHYL-ALPHA-AMINO-GAMMA-OXO-GAMMA-PHENYBUTYRATE DERIVATIVES

[75] Inventors: Satomi Takahashi, Kobe; Yasuyoshi Ueda, Takasago; Kazuhiko Yamada, Akashi; Yukio Yamada, Kakogawa; Takehiko Yamane, Akashi; Yoshifumi Yanagita, Takasago; Yoshio Shimada, Kakogawa; Kiyoshi Watanabe, Akashi; Michio Nomura, Takasago; Takehisa Ohashi; Kenji Inoue, both of Kobe, all of Japan

[73] Assignee: Kanegafuchi Kagaku Kogyo Kabushiki Kaisha, Osaka, Japan

[21] Appl. No.: 324,497

[22] Filed: Mar. 16, 1989

Related U.S. Application Data

[63] Continuation-in-part of Ser. No. 289,421, Dec. 23, 1988, abandoned, and Ser. No. 246,007, Sep. 15, 1988, abandoned, which is a continuation-in-part of Ser. No. 28,939, Mar. 23, 1987, abandoned, said Ser. No. 289,421, is a continuation of Ser. No. 201;349, Jun. 1, 1988, abandoned, which is a continuation of Ser. No. 825,287, Feb. 3, 1986, abandoned.

[30] Foreign Application Priority Data

Feb. 4, 1985 [JP] Japan ................... 60-19483
Aug. 12, 1985 [JP] Japan ................... 60-178396
Mar. 27, 1986 [JP] Japan ................... 61-68970

[51] Int. Cl.$^5$ .......................... C07C 101/10
[52] U.S. Cl. ......................... 560/41; 560/38
[58] Field of Search ..................... 560/38, 41

[56] References Cited

U.S. PATENT DOCUMENTS 4,626,545 12/1986 Taub ..................... 574/423
4,727,160 2/1988 Teetz et al. ............... 548/452

FOREIGN PATENT DOCUMENTS 3226768 6/1983 Fed. Rep. of Germany .
42-17893 9/1967 Japan .
51-56418 5/1976 Japan .
58-103364 6/1983 Japan .
61-36297 2/1986 Japan .

OTHER PUBLICATIONS

Chemical Abstracts, vol. 99, Abstract No. 15884k (1983).
Bergmann et al., *Organic Reactions*, John Wiley & Sons, New York, vol. 10, pp. 179-191 (1959).
Chemical Abstracts, vol. 89, Abstract No. 215732p (1978); and Agbalyan et al., Arm. Khim. Zh., vol. 31, No. 4, pp. 273-275 (1978).
Chemical Abstracts, vol. 107, Abstract No. 59477s (1987).
McOmie, *Protective Groups in Organic Chemistry*, Plenum Press, London, pp. 46-51 and 83-87 (1973).

*Primary Examiner*—Bruce D. Gray
*Attorney, Agent, or Firm*—Armstrong, Nikaido, Marmelstein, Kubovcik & Murray

[57] ABSTRACT

Ethyl-$\beta$-benzoyacrylate is reacted with an alkali metal salt of (S)-alanine or an alkali metal salt of $N^6$-trifluoroacetyl-L-lysine to form the corresponding Michael addition product, and not less than an equivalent amount of acid is added after completion of the Michael addition to prevent conversion of the (S,S) form of the product to the (R,S) form.

14 Claims, No Drawings

PROCESS FOR PREPARING ETHYL-ALPHA-AMINO-GAMMA-OXO-GAMMA-PHENYBUTYRATE DERIVATIVES

This application is a continuation-in-part of application Ser. No. 289,421 filed Dec. 23, 1988 now abandoned (which is a continuation of application Ser. No. 201,349, filed June 1, 1988 and now abandoned, which is in turn a continuation of application Ser. No. 825,287, filed Feb. 3, 1986 and now abandoned). This application is also a continuation-in-part of application Ser. No. 246,007 now abandoned, filed Sept. 15, 1988 (which is a continuation-in-part of application Ser. No. 028,939, filed Mar. 23, 1987, and now abandoned).

BACKGROUND OF THE INVENTION

A first aspect of the present invention, which was originally disclosed in application Ser. No. 825,287, relates to a process for preparing ethyl-α-(1-carboxyethyl)amino-γ-oxo-γ-phenylbutyrate, especially its optically active (αS,1S)-form having the formula (I):

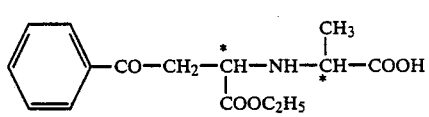

wherein the asterisk represents the (S)-configuration at the asymmetric carbon atom.

The compound having the formula (I) is a precursor of ethyl-(αS,1S)-α-(1-carboxyethyl)amino-γ-phenylbutyrate having the formula (III):

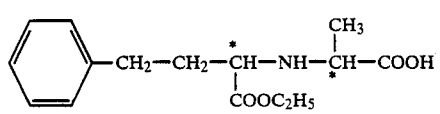

wherein the asterisk represents the (S)-configuration at the asymmetric carbon atom, which is a very useful intermediate compound for synthesis of the various amino acid derivatives having the formula (II):

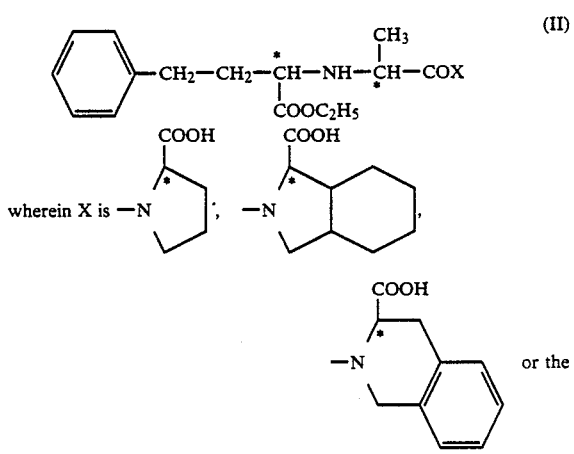

like, and the asterisk represents the (S)-configuration at the asymmetric carbon atom, said amino acid derivatives having the general formula (II) being expected to be useful as antihypertensive agents due to their angiotensin converting enzyme (ACE) inhibitory activity.

Hitherto, it has been known that ethyl-α-(1-carboxyethyl)amino-γ-oxo-γ-phenylbutyrate can be prepared by subjecting ethyl-β-benzoylacrylate (IV) and the (S)-alanine benzyl ester (V) to the so-called Michael addition reaction in the presence of triethylamine and then conducting hydrogenolysis of the product to cleave the benzyl group (Japanese Unexamined Patent Publication No. 103364/1983, U.S. Pat. No. 4,727,160 and Tetrahedron Letters, Vol. 25 (11), 1143, (1984)). The reaction scheme is as follows:

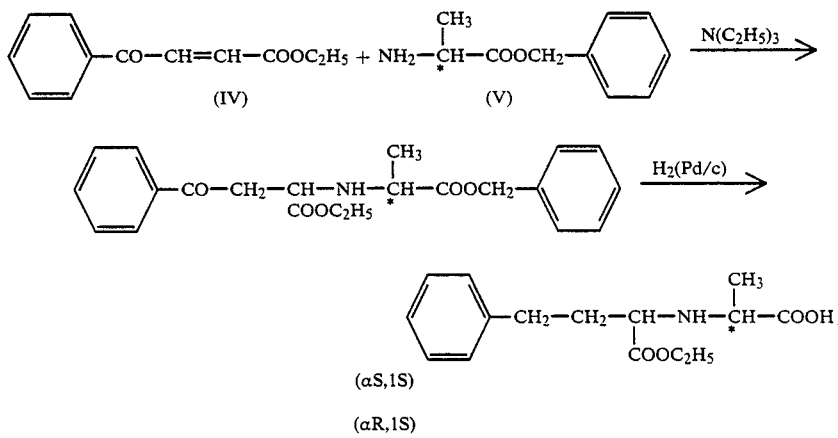

It is also confirmed that the (αS,1S)-diastereoisomer (VI) is predominantly produced when the (S)-alanine ester is employed, and thus the (αS,1S)-diastereoisomer (VI) can be obtained by crystallization or silica gel column chromatography. However, the above method employing the (S)-alanine ester requires a procedure for converting the amino group moiety of the ester, which is present in the form of a salt with an acid used in the esterification, into a free amino group, in addition to a procedure for esterifying the (S)-alanine. Further, it is required to employ such an ester that the ester moiety is selectively converted into a carboxylic group by hydrogenolysis without converting the ethyl ester moiety of the product derived from ethyl-β-benzoylacryrate into a carboxylic group. Thus the ester which can be employed in the reaction is limited to esters such as benzyl ester of tert-butyl ester, which are prepared by a relatively complicated procedure. Moreover, in order to carry out a selective ester degradation, a complicated procedure such as hydrogenolysis or trifluoroacetic acid treatment is required. Consequently, it is understood that the method is not suitable for industrial production of (αS,1S)-ethyl-α-(1-carboxyethyl)amino-γ-oxo-γ-phenylbutyrate, from the viewpoint of operability and cost of production.

As the result of the present inventors' continuous efforts to develop an economical, simple and efficient process for industrial production of (αS,1S)-ethyl-α-(1-carboxyethyl)amino-γ-oxo-γ-phenylbutyrate, it was found that ethyl-α-(1-carboxyethyl) amino-γ-oxo-γ-phenylbutyrate can be obtained in an extremely high yield by reaction an alkali metal salt, an alkaline earth metal salt or a quarternary ammonium salt of alanine with ethyl-β-benzoylacrylate, that the (αS,1S)-diastereoisomer of ethyl-α-(1-carboxyethyl) amino-γ-oxo-γ-phenylbutyrate is predominantly formed over the (αR,1S)-diastereoisomer by conducting the reaction under particularly controlled reaction conditions employing a metal salt of (S)-alanine, that the (αS,1S)-form is selectively crystallized only by adding an equivalent amount of an acid for neutralization, and the almost pure (αS,1S)-form is obtained by a simple procedure with an excellent high yield, and that ethyl-α-(1-carboxyethyl)amino-γ-phenylbutyrate can be prepared by catalytically reducing ethyl-α-(1-carboxyethyl) amino-γ-oxo-γ-phenylbutyrate.

A second aspect of the present invention, which was originally disclosed in application Ser. No. 028,939, aims at preparing in an industrially advantageous manner an N2-[1-(S)-carboxy-3-phenylpropyl]-L-lysine derivative which is a useful intermediate for preparing N2-[1-(S)-carboxy-3-phenylpropyl]-L-lysyl-L-proline having the formula (VIII):

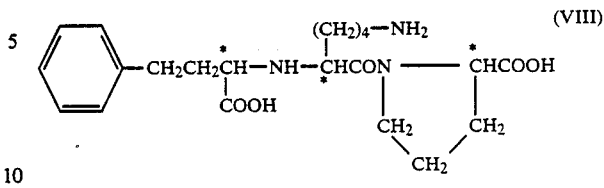

wherein the asterisk (*) represents the (S)-configuration with respect to the asymmetric carbon atom, which is expected to be useful as an antihypertensive agent because the proline has an excellent angiotensin converting enzyme (ACE) inhibitory activity.

In a known process for preparing N2-(1-carboxy-3-phenylpropyl)-L-lysine derivatives, ethyl-β-benzoylacrylate (IV) is reacted with the L-lysine ester derivative, N6-benzyloxy-carbonyl-L-lysine benzyl ester (IX), by the so-called Michael addition reaction in the presence of a catalytic amount of triethylamine to give a diastereomeric mixture of the N2-(1-ethoxycarbonyl-3-oxo-3-phenylpropyl)-N6-benzyloxycarbonyl-L-lysine benzyl ester (X), from which the N2-(1-(S)-ethoxycarbonyl-3-oxo-3-phenylpropyl)-N6-benzyloxycarbonyl-L-lysine benzyl ester (X-a) having the desired configuration is obtained by crystallization, the ester (X-a) being subjected to catalytic reduction with a palladium/carbon catalyst to give N2-(1-(S)-ethoxycarbonyl-3-phenylpropyl)-L-lysine (XI), followed by reaction with chloroformic acid benzyl ester in order to protect the amino group at the side chain of the lysine, and purification of the product by silica-gel chromatography to give N2-(1-(S)-ethoxycarbonyl-3-phenylpropyl)-N6-benzyloxycarbonyl-L-lysine (XII), as shown in the following reaction scheme (Japanese Unexamined Patent Publication No. 103364/1983 and U.S. Pat. No. 4,727,160):

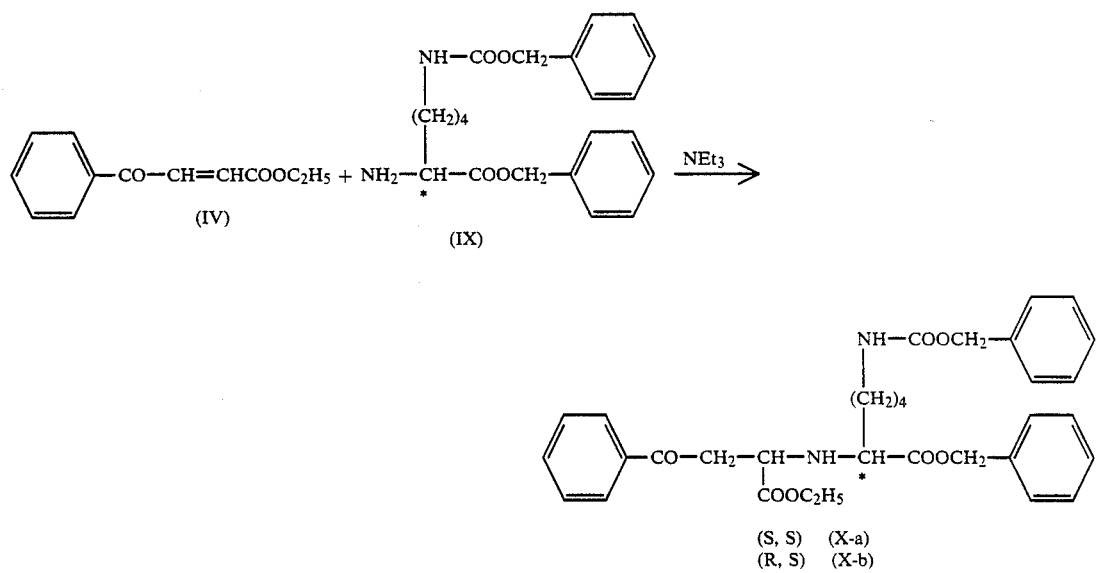

-continued

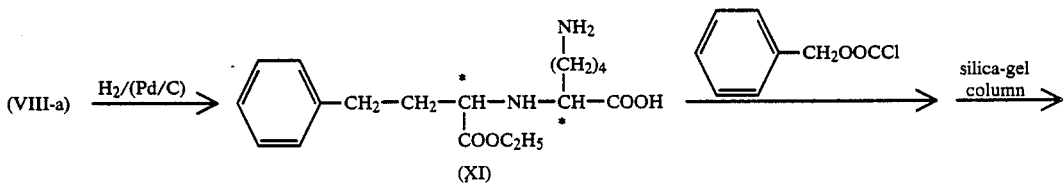

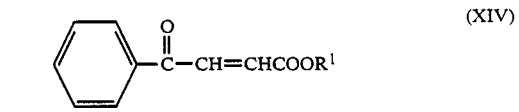

However, the above method employing the L-lysine ester derivative requires a procedure for converting the α-amino group moiety of the N⁶-benzyloxycarbonyl-L-lysine benzyl ester, which is present in the form of a salt with an acid used in the esterification, into a free amino group, in addition to a procedure for esterifying the L-lysine derivative. Further, it is required to employ an ester such that the ester moiety is selectively converted in to a carboxylic group without converting the ethyl ester moiety of the product derived from ethyl β-benzoylacrylate into a carboxylic group. Thus the ester which can be employed in the reaction is limited to esters such as benzyl ester or tert-butyl ester, which are prepared by a relatively complicated procedure. Since lysine is a basic amino acid having an amino group at the side chain, it is preferred that the amino group at the ε-position is protected by the protective group usually employed in the peptide synthesis in order to carry out the reaction of the amino group only at the α-position. When a benzyloxycarbonyl group is employed as the protective group, the amino group at the ε-position is deprotected by hydrogenolysis in the reduction of the compound (X-a) to the compound (XI). In order to use the compound (XI) in the subsequent reaction, the amino group at the ε-position in the lysine moiety is preferably protected, and thus the compound (XI) is reacted with the chloroformic acid benzyl ester to introduce a benzyloxycarbonyl group. However, since the amino group at the α-position is reactive as well as the amino group at the ε-position in the lysine moiety in the compound (XI), the production of by-product inevitably occurs. Therefore, the molar yield of the compound (XII) purified by silica gel chromatography is as low as 42% based on the compound (XI), and also the total molar yield is only 15.8% based on the starting N⁶-benzyloxycarbonyl-L-lysine benzyl ester. As mentioned above, the method gives a quite low yield with the employment of starting materials which are prepared in many steps and is not well suited for the production of the N²-(1-carboxy-3-phenylpropyl)-L-lysine derivative on an industrial scale, from the viewpoint of operability and economy.

As a result of the inventors' research, in light of the above-mentioned technical background, the inventors have now been found that an N²-[1-carboxy-3-oxo-3-phenylpropyl]-L-lysine derivative having the formula (XIII):

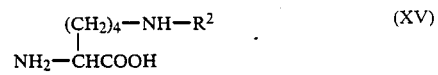

wherein $R^1$ is an alkyl group and $R^2$ is an acyl or urethane type protecting roup, can be obtained in extremely high yield by reacting a β-benzoylacrylic acid ester having the formula (XIV):

$$\underset{(XIV)}{\text{Ph}-\overset{O}{\underset{\|}{C}}-CH=CHCOOR^1}$$

wherein $R^1$ is an alkyl group, with an L-lysine derivative having the formula (XV):

$$\underset{(XV)}{\underset{NH_2-CHCOOH}{\overset{(CH_2)_4-NH-R^2}{|}}}$$

wherein $R^2$ is an acyl or urethane type protecting group which is stable upon catalytic hydrogenolysis in the presence of a base in an amount equivalent to the compound (XV), that the desired compound with the (S)-configuration with respect to the asymmetric carbon atom can be obtained in a large amount compared with the undesired compound with the (R)-configuration, by conducting the above-mentioned reaction under specific reaction conditions, and that an N²-(1-carboxy-3-phenylpropyl)-L-lysine derivative having the formula (XVI):

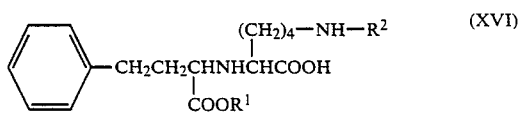

wherein $R^1$ and $R^2$ are as defined above, can be easily prepared by conducting catalytic hydrogenolysis of the lysine derivatives (XIII).

SUMMARY OF THE INVENTION

According to the first aspect of the present invention, there is provided a process for preparing ethyl-α-(1-carboxyethyl) amino-γ-oxo-γ-phenylbutyrate by reacting an alkali metal salt, an alkaline earth metal salt or a quarternary ammonium salt of alanine with ethyl-β-benzoylacrylate, wherein the (αS,1S)-diastereoisomer is obtained predominantly over the (αR,1S)-diastereoisomer by conducting the reaction under controlled conditions employing (S)-alanine, and a process for preparing ethyl-α-(1-carboxyethyl)amino-γ-phenylbutyrate by catalytically reducing ethyl-α-(1-carboxyethyl) amino-γ-oxo-γ-phenylbutyrate.

According to the second aspect of the present invention, there is provided a process for preparing an $N^2$-(1-carboxy-3-oxo-3-phenylpropyl)-L-lysine derivative having the formula (XIII):

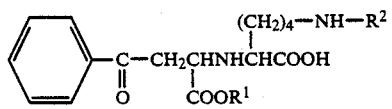

wherein $R^1$ is an alkyl group and $R^2$ is an acyl or urethane type protecting group, which comprises reacting a β-benzoylacrylic acid ester having the formula (XIV):

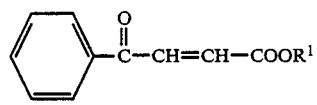

wherein $R^1$ is as defined above, with an L-lysine derivative having the formula (XV):

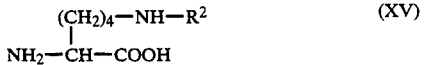

wherein $R^2$ is as defined above, in the presence of a base in an amount equivalent to the compound (XV), and a process for preparing an $N^2$-(1-carboxy-3-phenylpropyl)-L-lysine derivative having the formula (XVI):

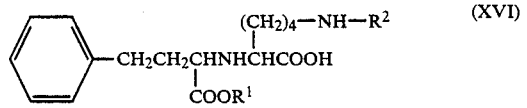

wherein $R^1$ and $R^2$ are as defined above, which comprises conducting catalytic hydrogenolysis of an $N^2$-(1-carboxy-3-oxo-3-phenylpropyl--L-lysine derivative having the formula (XIII):

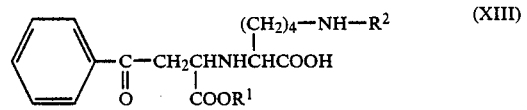

wherein $R^1$ and $R^2$ are as defined above.

DETAILED DESCRIPTION OF THE INVENTION

Preparation of ethyl-α-(1-carboxyethyl) amino-γ-oxo-γ-phenylbutyrate

The trans-ethyl-β-benzoylacrylate can be easily prepared, for instance, by ethyl esterification of trans-β-benzoylacrylic acid, which is obtained by a known method such a Friedel-Crafts' acylation reaction of benzene and maleic anhydride or dehydration condensation of glyoxalic acid and acetophenone. Cis-ethyl-β-benzoylacrylate can be prepared by isomerizing the trans-form with irradiation of light.

The alkali metal salt, alkaline earth metal salt or quarternary ammonium salt of alanine can be prepared by a simple procedure such as stirring a mixture of alanine and a stoichiometrically necessary amount of alkali metal hydroxide, alkaline earth metal hydroxide, alkali metal carbonate, quarternary ammonium hydroxide or an ion exchange resin having quarternary ammonium hydroxide as an exchange group, in a solvent of water or alcohols at room temperature or with heating. If necessary, a metal salt of alanine can be isolated by distilling away the solvent under reduced pressure. Alternatively, a metal salt or quarternary ammonium salt of alanine can be prepared in situ in the reaction system by adding an alkali metal hydroxide, alkaline earth metal hydroxide, alkali metal carbonate or quarternary ammonium hydroxide to a mixture of ethyl-β-benzoylacrylate and alanine.

Examples of the quarternary ammonium employed in the reaction are, for instance, tetraalkyl ammonium such as tetramethyl ammonium, tetraethyl ammonium, tetrapropyl ammonium, tetrabutyl ammonium, tetrapentyl ammonium, tetrahexyl ammonium or tetraoctyl ammonium; or benzyltrimethyl ammonium, benzyltriethyl ammonium, cetyltrimethyl ammonium, decyltrimethyl ammonium, ethyltrimethyl ammonium, octyltrimethyl ammonium, phenyltrimethyl ammonium, trimethylstearyl ammonium, β-hydroxyethyltrimethyl ammonium, trioctylmethyl ammonium, tetradecyldimethylbenzyl ammonium and the like. Ammonium is also employed in the reaction. Further, an anion exchange resin having a quarternary ammonium as an exchange group can also be employed though the reaction is carried out in a solid-liquid phase.

Michael addition reaction of ethyl-β-benzoylacrylate and an alkali metal salt, an alkaline earth metal salt or a quarternary ammonium salt of alanine can be carried out in a vast range of solvent such as, for instance, water, alcohols such as methanol, ethanol, propanol and butanol, chloroform, acetonitrile, n-hexane, dioxane, tetrahydrofuran or a mixture thereof. The reaction is usually carried out in a solvent of alcohols.

Except for the reaction in a heterogeneous system, the addition reaction in a homogeneous system employing a solvent of alcohols proceeds very rapidly and is usually completed within several minutes to one hour at room temperature. Though the reaction may be carried out at a temperature ranging from −10° to 60° C., it is not preferable to conduct the reaction at a higher temperature since the formed ethyl-α-(1-carboxyethyl) amino-γ-oxo-γ-phenylbutyrate is relatively unstable to the alkali in the reaction system. This unstability of the product in the reaction system is also observed after completion of the reaction as well as during the reaction, and with the passage of time a decreased content of the product and a change in the ratio of diastereoisomers are observed. However, such change of the product does not occur when the reaction system is acidified by adding not less than an equivalent amount of an acid based on the employed alkali, especially a mineral acid such as hydrochloric acid or sulfuric acid, to stabilize the product, which makes the subsequent operation much more easy.

The obtained ethyl-α-(1-carboxyethyl)amino-γ-oxo-γ-phenylbutyrate can be easily isolated in a conventional manner by neutralizing the alkali with an acid and distilling away the solvent under reduced pressure, followed by crystallization. If necessary, after distilling away the solvent under reduced pressure, water is added to the residue, which is then extracted with dichloromethane and the like at pH 3.5 to 5 to separate the product in a conventional manner. It is also possible to conduct the reduction of the product without isolation to give ethyl-α-(1-carboxyethyl)amino-γ-phenylbutyrate, which is then isolated.

Though the preferable reaction condition for selectively increasing the yield of the (αS,1S)-diasteroisomer in the Michael addition reaction of ethyl-β-benzoylacrylate and a metal salt or a quarternary ammonium salt of (S)-alanine varies depending on the combination of the agents employed in the reaction, it is mainly affected by factors such as the nature of the salt of (S)-alanine, the reaction procedure and the concentration of the agents in the reaction. Lithium, sodium, potassium, magnesium, barium or calcium employed as an alkali metal or an alkaline earth metal. However calcium is not suitable since it rather accelerates the production of the (αR,1S)-diastereoisomer. Though it is preferable to employ the lithium salt or potassium salt of (S)-alanine when the reaction solvent is ethanol, a different kind of (S)-alanine metal salt is employed depending on whether the trans-form or cis-form of ethyl-β-benzoylacrylate is employed. That is, the (αS,1S)-diastereoisomer is prepared in a higher yield by employing the lithium salt of (S)-alanine when trans-ethyl-α-benzoylacrylate is employed, and by employing the potassium salt of (S)-alanine when cis-ethyl-β-benzoylacrylate is employed.

As described above, the optimum condition varies extremely depending on the kind of isomer of ethyl-β-benzoylacrylate and cannot be stated broadly. In case the trans-form of ethyl-β-benzoylacrylate is used, preferably the lithium salt of (S)-alanine is slowly added for 5 minutes to 1 hour to an equivalent amount or an excess amount of ethyl-β-benzoylacrylate based on the lithium salt of (S)-alanine, and the reaction is preferably carried out in a relatively low concentration of 50 mM to 500 mM. On the other hand, in the case the cis-form of ethyl-β-benzoylacrylate is used, the potassium salt of (S)-alanine and ethyl-β-benzoylacrylate are preferably mixed together at a stretch in a higher concentration. When a quarternary ammonium salt of (S)-alanine is employed, an excess amount of ethyl-β-benzoylacrylate based on the quarternary ammonium salt of (S)-alanine is preferably employed, from the view point of the ratio of diastereoisomers and the yield. In any case, the addition reaction is completed with 5 minutes to 1 hour after completion of the addition of the reactants.

In comparing the use of the trans-form to the chaceform of ethyl-β-benzoylacrylate as a whole, there is a tendency that the trans-form gives a higher (αS,1S)-/(αR,1S) ratio than the chace-form. When the condition as described above is employed, it is possible to obtain a (αS,1S)/(αR,1S) ratio of 4 to 5 with the trans-form, and 2 to 3 with the cis-form.

After completion of the addition reaction, an acid such as hydrochloric acid or sulfuric acid is immediately added to the ammonium salt of ethyl-α-(1-carboxyethyl) amino-γ-oxo-γ-phenylbutyrate into ethyl-α-(1-carboxyethyl) amino-γ-oxo-γ-phenylbutyrate or hydrochloride or sulfate thereof, which is then isolated as a mixture of diastereoisomers. However, when ethanol is used as a solvent, only the optically almost pure (αS,1S)-diastereoisomer is crystallized by adding an equivalent amount of hydrochloric acid based on the alkali used and stirring the mixture while cooling the reaction mixture, and thus only the desired compound can be isolated in an extremely high yield. By this procedure, the complicated operation of optical resolution indispensable to a usual synthesis reaction is not required, and consequently (αS,1S)-ethyl-α-(1-carboxyethyl) amino-γ-oxo-γ-phenylbutyrate can be prepared very efficiently.

Alternatively, the reduction reaction can be carried out successively without isolation of the ethyl-α-(1-carboxyethyl) amino-γ-oxo-γ-phenylbutyrate after adding not less than an equivalent amount of sulfuric acid based on the alkali used in the addition reaction wherein ethanol is employed as a solvent. The catalytic reduction of ethyl-α-(1-carboxyethyl) amino-γ-oxo-γ-phenylbutyrate to ethyl-α-(1-carboxyethyl)amino-γ-phenylbutyrate proceeds with good yield in the presence of a small amount of an acid such as sulfuric acid, hydrochloric acid or phosphoric acid in a polar protic solvent such as, for instance, an alcohol, preferably ethanol, or a carboxylic acid such as acetic acid. Examples of suitable catalyst are, for instance, Raney nickel, palladium, platinum and the like.

For example, when palladium carbon is employed as a catalyst, around 2 to around 70% of palladium carbon based on the ethyl-α-(1-carboxyethyl) amino-γ-oxo-γ-phenylbutyrate is added to the reaction system, and the catalytic reduction is conducted in a solvent of alcohol such as ethanol at 0° to 50° C., preferably 20° to 40° C., for several hours to 30 hours to almost quantitatively produce ethyl-α-(1-carboxyethyl)amino-γ-phenylbutyrate. Also the reaction time can be shortened by increasing the amount of the catalyst.

After completion of the reaction, the catalyst is separated, the acid is neutralized with an alkali such as, for instance, sodium hydroxide and the solvent is distilled away, followed by optical resolution such as by recrystallization to give a highly pure crystal of (αR,1S)- or (αS,1S)-ethyl-α-(1-carboxyethyl)amino-γ-phenylbutyrate. When (αS,1S)-ethyl-α-(1carboxyethyl) amino-γ-oxo-γ-phenylbutyrate is used as a starting material, (αS,1S)-ethyl-α-(1-carboxyethyl)amino-γ-phenylbutyrate can be obtained.

According to the first aspect of the present invention, by controlling the conditions of the Michael addition reaction or the work-up thereof, as described above, (αS,1S)-ethyl-α-(1-carboxyethyl) amino-γ-oxo-γ-phenylbutyrate can be prepared in an extremely high yield starting from low-priced trans-ethyl-β-benzoylacrylate or cis-ethyl-β-benzoylacrylate and a metal salt or quarternary ammonium salt of (S)-alanine. Further, according to the first aspect of the present invention, (αS,1S)-ethyl-α-(1-carboxyethyl)amino-γ-phenylbutyrate, which is an important intermediate compound for preparing angiotensin converting enzyme (ACE) inhibitory agents, can be prepared quite simply and efficiently.

The product of the first aspect of the invention, as described above, is named ethyl-α-(1-carboxyethyl)amino-γ-oxo-γ-phenylbutyrate according to the nomenclature used in the disclosure of application Ser. No. 825,287. The same product would have the following name if it were named according to the nomenclature used in application Ser. No. 028,939: N-(1-(S)-ethoxycarbonyl-3-phenylpropyl)-L-alanine.

Conversely, the product of the second aspect of the invention, which was named as a derivative of L-lysine in application Ser. No. 028,939, would be named as a derivative of phenylbutyrate according to the nomenclature used in application Ser. No. 825,287.

The following Table presents the names of the product of the first aspect of the invention, and of a product of the second aspect of the invention, as named according to both nomenclature systems.

| Nomenclature System | Product of first aspect of invention |
|---|---|
| 825,287 | (αS,1S)-ethyl-α-(1-carboxyethyl) amino-γ-oxo-γ-phenylbutyrate |
| 028,939 | N-(1-(S)-ethoxycarbonyl-3-phenylpropyl-L-alanine |
| | Product of second aspect of invention |
| 825,287 | (αS,1S)-ethyl-α-(1-carboxy-5-trifluoro-acetylamino pentyl) amino-γ-oxo-γ phenylbutyrate |
| 028,939 | N²-[1-(S)-carboxy-3-oxo-3-phenylpropyl]-N⁶-trifluoroacetyl-L-lysine |

Preparation of ethyl-α-(1-carboxy-5-trifluoracetylaminopentyl) amino-γ-oxo-γ-phenylbutyrate The second aspect of the invention is shown in the following reaction scheme:

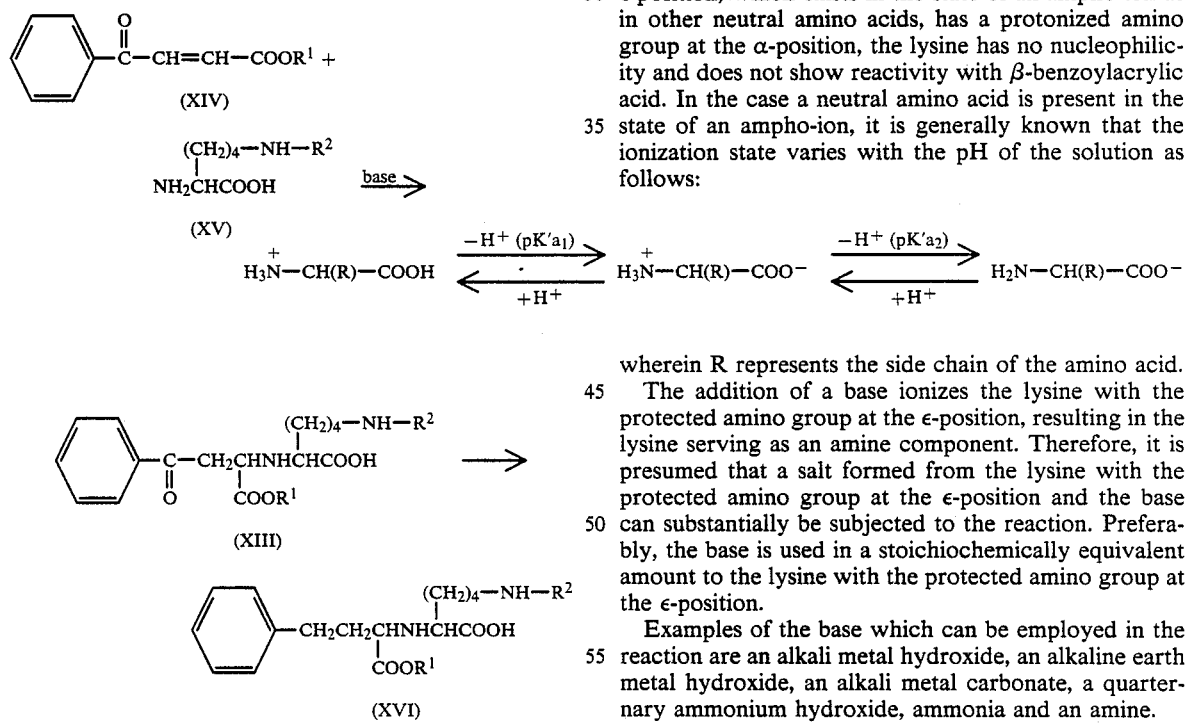

wherein R¹ is an alkyl group and R² is an acyl or urethane type protecting group which is stable upon catalytic hydrogenolysis.

As to the β-benzoylacrylic acid ester (XIV) used as a starting material, both the trans isomer and the cis isomer can be used in the present invention. However, the trans isomer, which is prepared in fewer steps than the cis isomer, is preferred from the point of industrial use.

Examples of the alkyl group are, for instance, methyl, ethyl, n-propyl, iso-propyl, n-butyl, tert-butyl and the like. The above groups having from 1 to 4 carbon atoms are preferable since they are stable upon catalytic hydrogenolysis. To the contrary, a group likely to be removed upon catalytic hydrogenolysis, e.g., benzyl, nitrobenzyl or methoxybenzyl, is not preferable.

The L-lysine derivatives (XV) used in the addition reaction of the present invention have two amino groups, at the α-position and ε-position of L-lysine. Accordingly, when the L-lysine derivatives in which the amino groups are not protected are used in the addition reaction, although the reaction can proceed, there is produced much by-product in which the amino group at the ε-position of the L-lysine is reacted with the β-benzoylacrylic acid ester, besides the desired compound in which the amino group at the α-position of L-lysine is added, and the ratio of the desired compound to the obtained product is about 50%. Therefore, in order to react only the amino group at the α-position with the β-benzoylacrylic acid ester, it is preferable to protect the amino group at the ε-position with a protecting group usually used in peptide synthesis, but which is stable on catalytic hydrogenolysis. Examples of such protecting group are, for instance, a urethane type protecting group such as tertiary butyloxycarbonyl (Boc), methylsulfonyl-ethyloxycarbonyl (Msoc), amyloxycarbonyl (Acc) or isobornyloxycarbonyl (Iboc), an acyl type protecting group such as trifluoroacetyl, formyl or phthaloyl and the like.

Since a lysine with a protected amino group at the ε-position, which exists in the state of an ampho-ion as in other neutral amino acids, has a protonized amino group at the α-position, the lysine has no nucleophilicity and does not show reactivity with β-benzoylacrylic acid. In the case a neutral amino acid is present in the state of an ampho-ion, it is generally known that the ionization state varies with the pH of the solution as follows:

$$H_3\overset{+}{N}-CH(R)-COOH \xrightleftharpoons[+H^+]{-H^+ (pK'_{a_1})} H_3\overset{+}{N}-CH(R)-COO^- \xrightleftharpoons[+H^+]{-H^+ (pK'_{a_2})} H_2N-CH(R)-COO^-$$

wherein R represents the side chain of the amino acid.

The addition of a base ionizes the lysine with the protected amino group at the ε-position, resulting in the lysine serving as an amine component. Therefore, it is presumed that a salt formed from the lysine with the protected amino group at the ε-position and the base can substantially be subjected to the reaction. Preferably, the base is used in a stoichiochemically equivalent amount to the lysine with the protected amino group at the ε-position.

Examples of the base which can be employed in the reaction are an alkali metal hydroxide, an alkaline earth metal hydroxide, an alkali metal carbonate, a quarternary ammonium hydroxide, ammonia and an amine.

Examples of the alkali metal hydroxide are, for instance, lithium hydroxide, sodium hydroxide, potassium hydroxide and the like. Examples of the alkali metal carbonate are, for instance, lithium carbonate, sodium carbonate, potassium carbonate, sodium hydrogencarbonate, potassium hydrogencarbonate and the like.

When the ε-amino group in the lysine is protected with a group which does not react with the above-mentioned bases, a salt can be easily prepared by a method in which the base and the lysine in which the ε-amino group is protected are stirred in a solvent such as water or an alcohol at room temperature or under heating, and then the obtained salt can be reacted with the benzoylacrylic acid derivative.

It is also possible to carry out the reaction mildly by preparing the salt in situ in the reaction system by adding a stoichiometrically necessary amount of the base to the mixture of β-benzoylacrylic acid ester and the ε-amino group-protected lysine.

An example of the lysine derivative having a protected amino group at the ε-position is ε-trifluoroacetyl-L-lysine, which may obtained by known methods of trifluoroacetylation of lysine, such as described in Schallenberg et al, *J. Amer. Chem. Soc.* 77, 2779 (1955); and Weygand, *Chem. Ber.* 89. 647 (1956).

When ethyl trans-β-benzoylacrylate is reacted with ε-trifluoroacetyl-L-lysine in ethanol-water, it is suitable to use lithium hydroxide, sodium hydroxide or potassium hydroxide as the alkali metal. Among them, when using the lithium hydroxide, the desired $N^2$-[1-(S)-ethoxycarbonyl-3-oxo-3-phenylpropyl]-$N^6$-trifluoroacetyl-L-lysine can be obtained with remarkably high selectivity, i.e., the ratio of the (S,S)-form/the (R,S)-form is 82/18. Also, the ratio between the diastereoisomers in the composition is scarcely changed at a temperature of not more than 10° C., practically from $-30°$ C. to 10° C., and preferably from $-5°$ C. to 10° C.

The addition reaction is carried out for several minutes (preferably about 5 minutes) to about 1 hour. At a low temperature, the reaction requires a longer time. As to time required for adding a base to form a salt of $N^6$-trifluoroacetyl-L-lysine in a reaction system, in some case, the base is added rapidly, and in some case, about 150 minutes is required.

After completing the addition reaction, the mineral acid such as hydrochloric acid or sulfuric acid is rapidly added to the reaction system to convert the alkali salt of $N^2$-[1-(S)-ethoxycarbonyl-3-oxo-3-phenylpropyl]-$N^6$-trifluoroacetyl-L-lysine into $N^2$-[1-ethoxycarbonyl-3-oxo-3-phenylpropyl]-$N^6$-trifluoroacetyl-L-lysine, or the hydrochloride or sulfate thereof, and the desired compound can be stably isolated in a usual manner. Also, it is possible to conduct the reduction reaction continuously without isolating the $N^2$-[1-ethoxycarbonyl-3-oxo-3-phenylpropyl]-$N^6$-trifluoroacetyl-L-lysine after adding hydrochloric acid or sulfuric acid in an amount greater than the equivalent of the alkali used in the addition reaction.

The $N^2$-(1-carboxy-3-oxo-3-phenylpropyl)-L-lysine derivative can be subjected to catalytic hydrogenolysis proceeding gently in water, an alcohol or a polar protic solvent such as acetic acid in the presence of a suitable amount of an acid such as sulfuric acid, hydrochloric acid or formic acid to give the $N^2$-(1-carboxy-3-phenylpropyl)-L-lysine derivative in a high yield. In catalytic hydrogenolysis, palladium, Raney nickel, and the like are examples of suitable catalysts. For instance, when $N^2$-[1-ethoxycarbonyl-3-oxo-3-phenylpropyl]-$N^6$-trifluoroacetyl-L-lysine is subjected to catalytic hydrogenolysis, the lysine derivative is hydrogenated in an alcohol (such as ethanol) as the solvent in the presence of the acid at a temperature of 0° C. to 60° C., preferably from 5° C. to 40° C. for several to 24 hours by using palladium/carbon as the catalyst to give almost quantitatively $N^2$-(1-ethoxycarbonyl-3-phenylpropyl)-$N^6$-trifluoroacetyl-L-lysine. After completing the hydrogenation, the catalyst is removed from the reaction mixture, the acid of the resulting solution is neutralized with an alkali, from which the solvent is distilled away, and then the desired compound having the (S,S)-configuration can be isolated in a usual manner such as extraction. If necessary, recrystallization can be conducted from the obtained reaction mixture.

The thus obtained the $N^2$-(1-carboxy-3-phenylpropyl)-L-lysine derivatives, especially the $N^2$-[1-(S)-carboxy-3-phenylpropyl]-L-lysine derivatives, can be easily converted into the lysinopril derivatives in a known manner applicable to peptide synthesis, such as the acid chloride method, NCA method, activated ester method or mixed anhydride method.

As aforementioned, in the present invention there can be economically obtained in a high yield the $N^2$-(1-carboxy-3-oxo-3-phenylpropyl)-L-lysine derivatives, especially the optically active $N^2$-[1-(S)-carboxy-3-oxo-3-phenylpropyl]-L-lysine derivatives and the corresponding reduced compounds, the derivatives being useful as intermediates for lysinopril, which is expected to be useful as an antihypertensive agent. The present invention provides a remarkably useful method in the economical and efficient industrial production of lysinopril.

The present invention is more particularly described by the following Examples and Reference Examples. However, it should be understood that the present invention is not limited to the Examples and Reference Examples and various changes and modifications can be made without departing from the scope and spirit of the present invention.

Preparation of ethyl-α-]1-carboxyethyl)-amino-γ-oxo-γ-phenylbutyrate and corresponding reduced derivative In the high performance liquid chromatography (HPLC) analysis conducted in the following examples, a sample solution was subjected to the analysis after sufficient acidification of the sample solution to be stabilized, since ethyl-α-[1-carboxyethyl)-amino-γ-oxo-γ-phenylbutylate is somewhat unstable under alkaline condition as previously described, and the (αS,1S)-diastereoisomer tends to be converted to the (αR,1S)-diastereoisomer thermodynamically.

The HPLC analysis was conducted as follows:
Column: Finepak SIL $C_{18}$ (made by Japan Spectroscopic Co., Ltd.) (4.6 mm ID×250 mm)
Mobile phase: 60 mM phosphate buffer (pH 2.5)/acetonitrile=85/15 (V/V)
Flow rate: 1.5 ml/min.
Detection: 210 nm
Internal standard: 5-benzylhydantoin The instance HPLC analysis can separate and measure diastereoisomers such as the (αS,1S) or the (αR,1S)-form of ethyl-α-(1-carboxyethyl)amino-γ-oxo-γ-phenylbutyate or ethyl-α-(1-carboxyethyl)amino-γ-phenylbutyrate, and the analysis in the Examples was conducted by this method.

EXAMPLE 1

A solution of 0.18 mmol of an alkali metal salt of (S)-alanine or 0.09 mmol of an alkaline earth metal salt of (S)-alanine dissolved in 0.5 ml of ethanol was quickly added to a solution of 37 mg of transethyl-β-benzoylacrylate (hereinafter referred to as "t-EBA") dissolved in 0.5 ml of ethanol at room temperature, and the mixture was stirred for 5 minutes. Then the reaction was stopped by adding an acid to the reaction mixture, and the HPLC analysis of the obtained product was conducted, which showed the production of ethyl-α-(1-carboxyethyl)-amino-γ-oxo-γ-phenylbutyrate as shown in Table 1.

TABLE 1

| Alkali metal or alkaline earth metal | Amount of ethyl-α-(1-carboxyethyl)-amino-γ-oxo-γ-phenylbutyrate | |
|---|---|---|
| | (αS,1S)-form (mg) | (αR,1S)-form (mg) |
| Li | 80.8 | 17.3 |
| Na | 27.8 | 21.4 |
| K | 31.6 | 18.5 |
| Ca | 9.7 | 19.9 |

EXAMPLE 2

A small test tube was charged with 30 mg of lithium salt of (S)-alanine and 2.5 ml of each solvent as shown in Table 2, to which 120 μl (135 mg) of t-EBA was added while stirring with a magnetic stirrer, and the addition reaction was carried out. Then the reaction was stopped by adding an acid to the reaction mixture and the HPLC analysis of the obtained product was carried out, which showed the production of ethyl-α-(1-carboxyethyl)-amino-γ-oxo-γ-phenylbutyrate as shown in Table 2.

TABLE 2

| Solvent | Reaction time | Amount of ethyl-α-(1-carboxyethyl)amino-γ-oxo-γ-phenylbutyrate | |
|---|---|---|---|
| | | (αS,1S)-form (mg) | (αR,1S)-form (mg) |
| Water-ethanol (1/1) | 10 minutes | 43.5 | 35.8 |
| Methanol | 10 minutes | 38.9 | 28.3 |
| Ethanol | 10 minutes | 46.5 | 35.2 |
| n-Propanol | 60 minutes | 43.5 | 37.1 |
| i-Propanol | 60 minutes | 33.6 | 10.7 |
| n-Butanol | 60 minutes | 33.4 | 32.8 |
| i-Butanol | 60 minutes | 24.1 | 19.2 |
| Chloroform | 15 hours | 22.5 | 25.1 |
| Acetonitrile | 15 hours | 5.7 | 7.7 |
| n-Hexane | 15 hours | 8.8 | 6.5 |
| Dioxane | 15 hours | 8.9 | 10.1 |
| Tetrahydrofuran | 15 hours | 9.1 | 12.7 |
| Ethyl acetate/ethanol (1/1) | 30 minutes | 49.0 | 35.1 |

EXAMPLE 3

A 100 ml three-neck round bottom flask was charged with 1.02 g of t-EBA, 223 mg of (S)-alanine and 30 ml of ethanol, and the mixture was stirred with a magnetic stirrer at room temperature. By continuously adding 20 ml of ethanol solution containing 60 mg of lithium hydroxide to this suspension for 30 minutes, the reaction mixture became gradually transparent and homogeneous. After stirring the mixture for 5 minutes, the reaction was stopped by adding 150 μl of sulfuric acid to the reaction mixture. The HPLC analysis of the obtained product was carried out, which showed the production of 676 mg of ethyl-α-(1-carboxyethyl)-amino-γ-oxo-γ-phenylbutyrate ((αS,1S)-form/(αR,1S)-form)=65/35).

EXAMPLE 4

There was quickly added a solution of 46 mg of potassium salt of (S)-alanine dissolved in ethanol in an amount as shown in Table 3 to 73 mg of t-EBA at room temperature, and the mixture was stirred for 5 minutes. The HPLC analysis of the obtained product was carried out as in Example 1.

The results are shown in Table 3.

TABLE 3

| Amount of ethanol (concentration) | Amount of ethyl-α-(1-carboxyethyl)-amino-γ-oxo-γ-phenylbutyrate | |
|---|---|---|
| | (αS,1S)-form (mg) | (αR,1S)-form (mg) |
| 0.3 ml (1.08 mol/l) | 41.6 | 47.2 |
| 1.0 ml (0.36 mol/l) | 52.2 | 38.7 |
| 3.0 ml (0.11 mol/l) | 54.5 | 28.7 |

EXAMPLE 5

There was added a solution of 34 mg of lithium salt of (S)-alanine dissolved in 1 ml of ethanol to 73 mg of t-EBA at room temperature at an addition rate as shown in Table 4, and the mixture was stirred for 3 minutes. The HPLC analysis of the obtained product was carried out as in Example 1.

The results are shown in Table 4.

TABLE 4

| Addition rate | Amount of ethyl-α-(1-carboxyethyl)-amino-γ-oxo-γ-phenylbutyrate | |
|---|---|---|
| | (αS,1S)-form (mg) | (αR,1S)-form (mg) |
| 1 ml/sec | 56.5 | 36.6 |
| 0.3 ml/min | 62.7 | 24.6 |

EXAMPLE 6

There was added a solution of 46 mg of potassium salt of (S)-alanine dissolved in 1 ml of ethanol to a solution of 73 mg of t-EBA dissolved in ethanol of an amount as shown in Table 4 at room temperature for 3 minutes, and the mixture was stirred for 3 minutes. The HPLC analysis of the obtained product was carried out as in Example 1.

The results are shown in Table 5.

TABLE 5

| Amount of ethanol (concentration) | Amount of ethyl-α-(1-carboxyethyl)-amino-γ-oxo-γ-phenylbutyrate | |
|---|---|---|
| | (αS,1S)-form (mg) | (αR,1S)-form (mg) |
| 0.5 ml (0.78 mol/l) | 54.2 | 34.9 |
| 1.0 ml (0.36 mol/l) | 59.2 | 31.4 |
| 2.0 ml (0.18 mol/l) | 62.7 | 29.0 |

EXAMPLE 7

The procedure of Example 1 was repeated except that chace-ethyl-β-benzoylacrylate (hereinafter referred to as "c-EBA") was employed in place of t-EBA.

The results are shown in Table 6.

TABLE 6

| Alkali metal or alkaline earth metal | Amount of ethyl-α-(1-carboxyethyl)-amino-γ-oxo-γ-phenylbutyrate | |
|---|---|---|
| | (αS,1S)-form (mg) | (αR,1S)-form (mg) |
| Li | 12.0 | 24.9 |
| Na | 22.9 | 19.3 |
| K | 29.3 | 15.5 |
| Ca | 11.1 | 19.6 |

EXAMPLE 8

There was added a solution of 18 mg of lithium salt of (S)alanine dissolved in 1.5 ml of ethanol to a solution of 114 mg of c-EBA dissolved in 3 ml of ethanol at room temperature for 5 minutes, and the resultant was stirred for 3 minutes. The procedure of Example 1 was repeated and the HPLC analysis of the obtained product was carried out, which showed the production of 23 mg of ethyl-α-(1-carboxyethyl)amino-γ-oxo-γ-phenylbutyrate ((αS,1S)-form/(αR,1S)-form=50/50).

EXAMPLE 9

There was quickly added a solution of 118 mg of potassium salt of (S)-alanine dissolved in 0.5 ml of ethanol to a solution of 190 mg of c-EBA dissolved in 0.5 ml of ethanol at room temperature, and the mixture was stirred for 3 minutes. The HPLC . analysis of the obtained product was carried out as in Example 1, which showed the production of 245 mg of ethyl α-(1-carboxyethyl)amino-γoxo-γ-phenylbutyrate ((αS,1S)-form/(αR,1S)-form=69/31).

EXAMPLE 10

There was added a solution of 0.603 g of lithium salt of (S)-alanine dissolved in 42.6 ml of ethanol to a solution of 2.59 g of t-EBA dissolved in 77 ml of ethanol at room temperature for 30 minutes. After completion of the addition, the mixture was stirred for 5 minutes and 0.529 ml of concentrated hydrochloric acid was added, which was then cooled with ice water and the crystallization was carried out by adding 67.9 mg of the (αS,1S)-form of the product as seeds to the reaction mixture and stirring. After 4 hours, the precipitated crystals were filtered, washed with ethanol and dried to give 1.27 g of ethyl-α-(1-carboxyethyl)amino-γ-oxo-γ-phenylbutyrate ((αS,1S)-form/(αR, 1S)-form=95/5).

Melting point: 200° to 225° C. (dec.).

$^1$H-nuclear magnetic resonance spectrum (DMSO-d6): 1.0 to 1.4 (t,6H), 3.2 to 5.0 (m,8H) and 7.3 to 8.1 (m,5H).

Infrared absorption spectrum (cm$^{-1}$) (KBr disk): 3070, 1735, 1680, 1620 and 1580.

$[α]_D^{23}$ = +26.8 (c=1.0, 1N HCl).

EXAMPLE 11

There was quickly added a solution of 422 mg of potassium salt of (S)-alanine dissolved in 1.8 ml of ethanol to a solution of 680 mg of c-EBA dissolved in 1.8 ml of ethanol at room temperature, and the mixture was stirred for 3 minutes. The reaction was stopped by adding 327 mg (3.3 mmol) of H$_2$SO$_4$ to the reaction mixture, and the resultant was distributed between water and hexane. To the water layer was added 333 mg of triethylamine and the resultant extracted with dichloromethane three times. After dehydration of the dichloromathane layer with anhydrous magnesium sulfate, the solvent was removed by evaporation, followed by sufficient drying under reduced pressure to give 507 mg of ethyl-α-(1-carboxyethyl)amino-γ-oxo-γ-phenylbutylate ((αS,1S)-form/(αR,1S)-form=73/27).

EXAMPLE 12

There was dissolved 0.4 g of ethyl-α-(1-carboxyethyl)amino-γ-oxo-γ-phenylbutyrate prepared in Example 10 into 8.0 ml of 1.6% (v/v) H$_2$SO$_4$-AcOH, to which 0.1 g of 10% Pd/C was added and the hydrogenation reaction was carried out at room temperature under atmospheric pressure. After completion of the reaction, the catalyst was filtered off with suction, to which 2.5 ml of 1N NaOH solution was added and the resultant was concentrated under reduced pressure. After the residue was dissolved in water, the solution was adjusted to pH 3.0 and extracted with dichloromethane, the organic layer being washed with a saturated sodium chloride solution and concentrated under reduced pressure. The residue was crystallized from ethyl acetate to give 0.25 g of ethyl-α-(1-carboxyethyl)amino-γ-phenylbutyrate ((αS,1S)-form/(αR,1S)-form=99/1).

Melting point: 149° to 149.5° C.

$^1$H-Nuclear magnetic resonance spectrum (CDCl$_3$): 1.1 to 1.4 (t,3H), 1.4 to 1.6 (d,3H), 1.9 to 2.3 (m,2H), 2.5 to 2.9 (m,2H), 3.2 to 3.7 (m,2H), 4.0 to 4.4 (q,2H) and 6.9 to 7.4 (m,5H).

Infrared absorption spectrum (cm$^{-1}$) (KBr disk): 3030, 2950, 1740 and 1600.

$[α]_D^{23}$ = +29.3 (c=1.0, MeOH).

EXAMPLE 13

There was dissolved 0.20 g of ethyl-α-(1-carboxyethyl)amino-γ-oxo-γ-phenylbutyrate prepared in Example 10 into 11.0 ml of 1% (v/v) H$_2$SO$_4$-EtOH, to which 0.05 g of 10% Pd/C was added and the hydrogenation reaction was carried out at room temperature under atmospheric pressure. After completion of the reaction, the catalyst was filtered off with suction and the ethanol solution was neutralized with sodium hydroxide, followed by distillation of the solvent under reduced pressure. The residue was dissolved in water and extracted with dichloromethane, the organic layer being concentrated under reduced pressure. The residue was crystallized from ethyl acetate to give 0.152 g of ethyl-α-(1-carboxyethyl)amino-γ-phenylbutyrate ((αS,1S)-form/(αR,1S)-form=99/1).

EXAMPLE 14

There was added a solution of 2.4 g of lithium salt of (S)alanine dissolved in 160 ml of ethanol to 10.2 g of t-EBA dissolved in 300 ml of ethanol at room temperature for 30 minutes, and the mixture was stirred for 5 minutes. The reaction was stopped by adding 4.4 g of sulfuric acid and the ethanol solution was concentrated under reduced pressure by distillation of ethanol. The residue was washed with n-hexane, to which 150 ml of acetic acid was added to dissolve the residue. To the resultant was added 1.65 g of 10% Pd/C and the hydrogenation reaction was carried out at room temperature under atmospheric pressure. After completion of the reaction, the catalyst was filtered off with suction. To the sulfuric acid-acetic acid solution was added 44.9 ml of 1N NaOH and the resultant was concentrated under reduced pressure. After the residue was dissolved in water, the solution was adjusted to pH 3 and extracted with 300 ml of dichloromethane, the organic layer being washed with a saturated sodium chloride solution and concentrated under reduced pressure. The residue was crystallized from ethyl acetate to give 4.0 g of ethyl-α-(1-carboxyethyl)amino-γ-phenylbutyrate ((αS,1S)-form/(αR,1S)-form=95/5).

EXAMPLE 15

There was added a solution of 143.6 mg of lithium salt of (S)-alanine dissolved in 10 ml of ethanol to a solution of 616.0 mg of t-EBA dissolved in 18.2 ml of ethanol at room temperature for 30 minutes and the mixture was stirred for 5 minutes, each 5 ml of which was put into a test tube, to which hydrochloric acid or sulfuric acid was added. The stability of the product with the passage of time was examined by HPLC analysis.

The results are shown in Table 7.

TABLE 7

| Acid | Amount (mmole) | | Time (hour) | | |
|---|---|---|---|---|---|
| | | | 0 | 2 | 4 |
| HCl | 0.264 | (αS,1S)-form | 51.6 mg | 39.9 mg | 28.1 mg |
| | | (αR,1S)-form | 14.9 mg | 13.0 mg | 11.5 mg |
| HCl | 0.528 | (αS,1S)-form | 51.6 mg | 51.3 mg | 51.5 mg |
| | | (αR,1S)-form | 14.9 mg | 14.8 mg | 14.7 mg |
| H₂SO₄ | 0.132 | (αS,1S)-form | 51.6 mg | 32.4 mg | 16.5 mg |
| | | (αR,1S)-form | 14.9 mg | 10.8 mg | 10.1 mg |
| H₂SO₄ | 0.264 | (αS,1S)-form | 51.9 mg | 51.4 mg | 51.5 mg |
| | | (αR,1S)-form | 14.9 mg | 14.8 mg | 14.8 mg |
| no addition | | (αS,1S)-form | 51.9 mg | 37.9 mg | 29.3 mg |
| | | (αR,1S)-form | 14.9 mg | 25.3 mg | 30.5 mg |

EXAMPLE 16

There was added a solution of 0.332 g of lithium salt of (S)-alanine dissolved in 23 ml of ethanol to a solution of 1.42 g of t-EBA dissolved in 42 ml of ethanol at room temperature for 20 minutes. After completion of the reaction, the mixture was stirred for 3 minutes and 0.29 ml of concentrated hydrochloric acid was added, which was then cooled with ice water. The crystallization was carried out by adding 20 mg of the (αR,1S)form of the product as seeds. After 4 hours, the crystals were filtered off, washed with EtOH and dried to give 611 mg of ethyl-α-(1 1-carboxyethyl)amino-γ-oxo-γ-phenylbutyrate ((αS,1S)-form/(αR,1S)-form=96/4)).

Melting point: 202° to 220° C. (dec.).

$^1$H-Nuclear magnetic resonance spectrum (DMSO-d6): 1.0 to 1.4 (t,6H), 3.2 to 5.0 (m,8H) and 7.3 to 8.1 (m,5H).

Infrared absorption spectrum (cm$^{-1}$) (KBr disk): 3070, 1735, 1680,1620 and 1580.

$[\alpha]_D^{23} = -26.7$ (C=1.0, 1N HCl)

REFERENCE EXAMPLE 1

[Preparation of ethanol solution of a quarternary ammonium salt of (S)-alanine]

There was dissolved 25 mmole of various quarternary ammonium chloride into 12.5 ml of ethanol, to which 12.5 ml of ethanol solution containing 1.05 g (25 mmole) of sodium hydroxide was added and the mixture was sufficiently stirred. The formed NaCl precipitate was filtered to be removed. To the quarternary ammonium hydroxide solution 2.225 g (25 mmole) of the pulverized (S)-alanine was added and the mixture was stirred to form the salt, from which 50 ml of solution of the salt was prepared with ethanol (concentration: 0.5 M).

REFERENCE EXAMPLE 2

[Preparation of (S)-alanine carrier resin]

100 ml of the most strongly basic anion exchange resin was activated with 1N NaOH and sufficiently washed with water, to which 500 ml of an aqueous solution of 19.2 g of (S)-alanine was passed through, washed with water, and finally substituted with 150 ml of ethanol.

EXAMPLE 17

A 50 ml three-neck flat bottom flask was charged with 1.75 g (8.6 mmole) of t-EBA and 25 ml of ethanol, to which 8.6 ml (4.3 mmole) of an ethanol solution of a salt of (S)-alanine with quarternary ammonium as shown in Table 8 was continuously added at room temperature for 10 minutes while stirring with a magnetic stirrer, and the mixture was further stirred for 6 minutes. There was added 0.5 ml of the obtained solution to 10 ml of 0.05 N HCl solution containing 10 mg of 5-benzylhydantoin of a product was carried out, which showed the production of ethyl-α-(1-carboxyethyl)amino-γ-oxo-γ-phenylbutyrate as shown in Table 8.

TABLE 8

| | Amount of ethyl-α-(1-carboxyethyl)amino-γ-oxo-γ-phenylbutyrate | |
|---|---|---|
| Quarternary ammonium salt of (S)-alanine | (αS,1S)-form (mg) | (αR,1S)-form (mg) |
| Ammonium | 352.5 | 236.9 |
| Tetramethyl ammonium | 898.8 | 473.8 |
| Tetraethyl ammonium | 896.8 | 421.7 |
| Cetyltrimethyl ammonium | 837.3 | 415.0 |
| Trioctylmethyl ammonium | 824.2 | 429.1 |
| Tetra-n-butyl ammonium | 881.3 | 449.6 |
| Benzyltriethyl ammonium | 838.3 | 440.5 |
| Tetradecyldimethylbenzyl ammonium | 860.5 | 453.6 |
| Trimethylphenyl ammonium | 804.4 | 421.3 |
| Benzyldimethylphenyl ammonium | 608.5 | 320.5 |

EXAMPLE 18

There was mixed 1.75 g of t-EBA and 383 g of (S)-alanine with 25 ml of ethanol. By adding continuously 8.6 ml of ethanol solution containing 907 mg of benzyltriethyl ammonium hydroxide to the above suspension at room temperature for 15 minutes while stirring, the reaction mixture became gradually transparent and homogeneous. After stirring for 6 minutes, the HPLC analysis of the product was carried out as in Example 17, which showed the production of 948.1 mg of ethyl-α-(1-carboxyethyl)amino-γ-oxo-γ-phenylbutyrate ((αS,1S)-form/(αR,1S)-form=67.3/32.7).

EXAMPLE 19

There was suspended 1.75 g of t-EBA in 25 ml of water-ethanol (1:1), to which 8.6 ml of water-ethanol solution containing 4.3 mmole of ammonium salt of (S)-alanine was continuously added for 10 minutes. After stirring for 30 minutes, the HPLC analysis was carried out as in Example 17, which showed the production of 639 mg of ethyl-α-(1-carboxyethyl)amino-γ-oxo-γ-phenylbutyrate ((αS,1S)-form/(αR,1S)-form=58.6/4I 4)).

EXAMPLE 20

There was dissolved 1.30 g of c-EBA in place of t-EBA in 20 ml of ethanol, to which 6.4 ml of the solution containing 3.2 mmole of tetramethyl ammonium salt of (S)-alanine as in Example 17 was continuously added at room temperature for 10 minutes. After stirring for 6 minutes, the HPLC analysis was carried out as in Example 17, which showed the production of 984.7 mg of ethyl-α-(1-carboxyethyl)amino-γ-oxo-γ-phenylbutyrate ((αS,1S)-form/(αR,1S)-form=46.1/53.9).

EXAMPLE 21

There was continuously added 8.6 ml of an ethanol solution containing 4.3 mmole of benzyltriethyl ammonium salt of (S)alanine to a solution of 1.75 g of t-EBA dissolved in 25 ml of ethanol at room temperature for 10 minutes, which was then stirred for 6 minutes. The reaction solution was cooled with ice water and adjusted to pH 4.5 with concentrated hydrochloric acid, to which 40 mg of the (αS,1S)-form of the product was added as seeds, and the crystallization was carried out while stirring. After 4.5 hours, the crystals were filtered off, washed with ethanol and dried to give 0.698 g of ethyl-α-(1-carboxyethyl)amino-γ-oxo-γ-phenylbutyrate ((αS,1S)-form/(αR,1S)-form=95.4/4.6).

Melting point: 200° to 225° C. (dec.).

$^1$H Nuclear magnetic resonance spectrum (DMSO-d6): 1.0 to 1.4 (t,6H), 3.2 to 5.0 (m,8H) and 7.3 to 8.1 (m,5H).

Infrared absorption spectrum (cm$^{-1}$) (KBr disk): 3070, 1735, 1680, 1620 and 1580.

$[\alpha]_D^{23} = +26.8$ (C=1.0, 1N HCl)

EXAMPLE 22

There was continuously added 9 ml of ethanol solution containing 4.5 mmole of tetramethyl ammonium salt of (S)-alanine to a solution of 1.83 g of t-EBA dissolved in 25 ml of ethanol at room temperature for 12 minutes while adjusting to the predetermined pH as shown in Table 9 with an ethanol solution containing 2% acetic acid, and the reaction was carried with stirring. After stirring for 9 minutes, the HPLC analysis was carried out as in Example 17, which showed the production of ethyl-α-(1-carboxyethyl)amino-γ-oxo-γ-phenylbutyrate as shown in Table 9.

TABLE 9

|    | Amount of ethyl-α-(1-carboxyethyl)-amino-γ-oxo-γ-phenylbutyrate | |
|----|----|----|
| pH | (αS,1S)-form (mg) | (αR,1S)-form (mg) |
| 11 | 833 | 437 |
| 12 | 867 | 437 |
| 13 | 636 | 311 |

EXAMPLE 23

An (S)-alanine carrier resin of an ion exchange resin (estimated alanine content: 380 mg) was suspended in ethanol containing 1.75 g of EBA to prepare 30 ml of suspension, and the reaction was carried out at room temperature for the reaction time as shown in Table 10, while stirring slowly with a magnetic stirrer. The suspension was filtered and the resin was washed with ethanol. The resultant resin was added to 10 ml of 1N-HCl and the mixture was stirred for 30 minutes, and eluted twice. To the obtained solution was added ethanol to give a total volume of 25 ml. The HPLC analysis was carried out as in Example 17, which showed the production of ethyl-α-(1-carboxyethyl)amino-γ-oxo-γ-phenylbutyrate as shown in Table 10.

TABLE 10

| Ion exchange resin | Amount of resin (ml) | Reaction time (minutes) | Amount of ethyl-α-(1-carboxyethyl)amino-γ-oxo-γ-phenylbutyrate (mg) | |
|---|---|---|---|---|
| | | | (αS,1S)-form | (αR,1S)-form |
| AMBER-LITE IRA-400 | 5 | 15 | 134.5 | 123.0 |
|  |  | 90 | 224.0 | 310.8 |
| AMBER-LITE IRA-410 | 4 | 15 | 41.5 | 31.5 |
|  |  | 90 | 70.0 | 80.3 |
| AMBER-LITE IRA-900 | 7.4 | 15 | 490.5 | 401.3 |
|  |  | 90 | 395.0 | 482.8 |
| AMBER- | 7.3 | 15 | 376.5 | 396.8 |
| LYST A-26 |  | 90 | 555.8 | 336.0 |

Preparation of N$^2$-(1-ethoxycarboxyl-3-oxo-3-phenylpropyl) N$^6$-trifluoroacetyl)-L-lysine and reduced derivative In the following examples, the quantitative analysis was done by high performance liquid chromatography (HPLC). As aforementioned, N$^2$-(1-carboxy-3-oxo-3-phenylpropyl)-L-lysine derivatives are slightly unstable under alkaline conditions and are thermodynamically easily changed from the (S,S) form to the (R,S) form. Therefore, the tested samples were analyzed after being acidified sufficiently so as not to change the ratio of the (S,S) form and the (R,S) form. The following conditions were applied to the analysis unless otherwise noted, and the (S,S) form and the (R,S) form were separated completely and determined. The ratio of solvent of the mobile phase was optically adjusted according to the polarity of the N$^2$-(1-carboxy-3-oxo-3-phenylpropyl-L-lysine derivatives.

Column: Finepak SIL C$_{18}$-5 (made by Japan Spectroscopic Co., Ltd.), 4.6 mm ID×250 mm
Mobile phase: 60 mm phosphate buffer (pH 2.5)/acetonitrile=75/25 (v/v)
Flow rate: 1.2 ml/min
Detection: 210 nm
Internal standard: 5-benzyl hydantoin

EXAMPLES 24 to 26

There was dissolved 40.8 mg of trans-ethyl β-benzoylacrylate (hereinafter referred to as "t-EBA") in 2.0 ml of a solution of ethanol and water in a volume ratio of 3:1, and then 48.4 mg of N$^6$-trifluoroacetyl-L-lysine (hereinafter referred to as "L-Lys (Tfa)") was added. And to the suspension 0.2 ml of a solution or suspension containing an alkali metal hydroxide (0.2 milimol) shown in Table 11 was added rapidly while cooling with ice at 0° C., and the resultant was stirred for 30 minutes. After stopping the reaction by adding 0.5 ml of 1N-HCl (0.5 mmol), the product was analyzed by HPLC and the formation of N$^2$-(1-ethoxycarbonyl-3-oxo-3-phenylpropyl)- N$^6$-trifluoroacetyl)-L-lysine was found.

The amounts of the obtained (S,S) form and (R,S) form are shown in Table 11.

REFERENCE EXAMPLE 3

The procedures in Examples 24 to 26 were repeated without any alkali metal hydroxide or alkali earth metal hydroxide.

The amounts of the obtained (S,S) form and (R,S) form are shown in Table 11.

TABLE 11

| Example No. or Reference Example No. | alkali metal | amount of the (S,S) form (mg) | amount of the (R,S) form (mg) |
|---|---|---|---|
| Ex. 24 | Li | 41.1 | 10.6 |
| Ex. 25 | Na | 38.8 | 12.6 |
| Ex. 26 | K | 42.6 | 13.7 |

TABLE 11-continued

| Example No. or Reference Example No. | alkali metal | amount of the (S,S) form (mg) | amount of the (R,S) form (mg) |
|---|---|---|---|
| Ref. Ex. 3 | — | 0 | 0 |

EXAMPLES 27 to 32

There was dissolved 40.8 mg of t-EBA in 2.0 ml of a solution of ethanol and water in a volume ratio of 3:1, and then 48.4 mg of L-Lys (Tfa) was added. And to the suspension of 0.2 ml of a solution containing the alkali metal hydroxide (0.2 mmol) shown in Table 2 was added rapidly at 20° C. or while cooling with ice at 0° C., and the resultant was stirred for 30 minutes. The product was analyzed in the same manner as in Example 24, and the formation of $N^2$-(1-ethoxycarbonyl-3-oxo-3-phenylpropyl)-$N^6$-trifluoroacetyl)-L-lysine was found.

The amounts of the obtained (S,S) form and (R,S) form are shown in Table 12.

TABLE 12

| Example No. | alkali metal | reaction temperature (°C.) | amount of the (S,S) form (mg) | amount of the (R,S) form (mg) |
|---|---|---|---|---|
| Ex. 27 | Li | 0 | 43.6 | 10.9 |
| Ex. 28 | | 20 | 37.6 | 11.9 |
| Ex. 29 | Na | 0 | 37.2 | 11.9 |
| Ex. 30 | | 20 | 37.3 | 15.3 |
| Ex. 31 | K | 0 | 39.8 | 12.8 |
| Ex. 32 | | 20 | 36.7 | 15.0 |

EXAMPLE 33

After 2.45 g of t-EBA was dissolved in 50.0 ml of a solution of ethanol and water in a volume ratio of 3:1 and 2.42 g of L-Lys (Tfa) was suspended therein, the reaction mixture was warmed to 30° C. And thereto 2.45 g of potassium carbonate was added rapidly and the reaction mixture was stirred. The stirring was continued for 60 minutes. It took 20 minutes to make the reaction mixture almost homogeneous. After completion of the stirring, the reaction was stopped by adding 1.67 ml of concentrated hydrochloric acid. The reaction mixture was analyzed by HPLC and the formation of 3.48 g of $N^2$-(1-ethoxycarbonyl-3-oxo-3-phenylpropyl)-$N^6$-trifluoroacetyl-L-lysine was found. The ratio of the produced diastereomer of the (S,S) form to the (R,S) form was 61.0/39.0.

After the solvent of this reaction mixture was distilled away under reduced pressure, 50 ml of ethanol was added to the obtained residue. And thereto 4.0 ml of 2.5N NaOH was gradually added by stirring while cooling with ice at 0° C., and then the solvent was distilled away under reduced pressure at room temperature. After the residue was extracted with ethyl acetate and filtered, the extracted solution was washed, dried with sodium sulfate, concentrated under reduced pressure, and crystallized by adding ether-n-hexane to it.

Consequently, 3.08 g of $N^2$-(1-ethoxycarbonyl-3-oxo-3-phenylpropyl)-$N^6$-trifluoroacetyl-L-lysine was obtained. The ratio of the (S,S) form/the (R,S) form was 60.5/39.5.

EXAMPLE 34

After 81.6 g of t-EBA was dissolved in 1.0 liter of a solution of ethanol and water in a volume ratio of 3:1 and 48.4 g of L-Lys (Tfa) was suspended therein, the reaction mixture was cooled with ice to 3° C. There was added dropwise 200.0 ml of a solution of 1N-LiOH over 20 minutes while stirring the mixture, and the stirring was continued for an additional 40 minutes after completion of the dropping. The reaction was stopped by adding 33.3 ml of concentrated hydrochloric acid, and the reaction mixture was analyzed by HPLC. The formation of 84.9 g of $N^2$-(1-ethoxycarbonyl-3-oxo-3-phenylpropyl)-$N^6$-trifluoroacetyl-L-lysine was found. The ratio of the (S,S) form/the (R,S) form was 78.0/220.

After the solvent of this reaction mixture was distilled away under reduced pressure, 500 ml of water and 500 ml of ethyl acetate were added to the residue. And thereto 82 ml of 2.5 N NaOH was gradually added with vigorous stirring at 0° C. (pH 4.7), and then the solution was separated between an aqueous and an organic phase.

The extracted ethyl acetate solution was washed, dried with sodium sulfate, concentrated under reduced pressure, and crystallized by adding ether-n-hexane to the residue.

Consequently, 75.8 g of $N^2$-(1-ethoxycarbonyl-3-oxo-3-phenylpropyl)-$N^6$-trifluoroacetyl-L-lysine was obtained in the form of crystals. The ratio of the (S,S) form/the (R,S) form was 79.9/21.0.

The obtained product had the following properties.
1H-NMR (90 MHz, $CDCl_3$+DMSO-$d_6$): 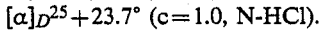 (ppm); 1.15 to 1.4 (t,3H), 0.9 to 1.9 (m,6H), 3.0 to 3.55 (m, 5H), 3.6 to 3.85 (m, 1H), 3.95 to 4.3 (q, 2H), 7.3 to 8.1 (m, 5H), 8.13 to 8.53 (m, 1H) IR (cm$^{-1}$, KBr disk): 3375, 2950, 1710, 1630, 1600, 1550, 1210, 1185, 690.
$[\alpha]_D^{25}$+23.7° (c=1.0, N-HCl).

EXAMPLE 35

After 40.8 g of t-EBA was dissolved in 500 ml of ethanol and 48.4 g of L-Lys (Tfa) was suspended therein, the reaction mixture was cooled to −5° C. And thereto 200.0 ml of a solution of 1N-LiOH was continuously dropped over 150 minutes while stirring the mixture, and the stirring was continued for an additional 30 minutes after the dropping was over. The internal temperature of reaction mixture was kept at −5° C. during the reaction.

After the reaction was stopped by adding 33.3 ml of concentrated hydrochloric acid, the reaction mixture was analyzed by HPLC, and the formation of 81.4 g of $N^2$-(1-ethoxycarbonyl-3-oxo-3-phenylpropyl)-$N^6$-trifluoroacetyl-L-lysine was found. The ratio of the (S,S) form/the (R,S) form was 82.1/17.9.

The obtained reaction mixture was treated in the same manner as in Example 33, and 65.0 g of $N^2$-(1-ethoxycarbonyl-3-oxo-3-phenylpropyl)-$N^6$-trifluoroacetyl-L-lysine was obtained in the form of crystals. The ratio of the (S,S) form/the (R,S) form was 81.9/18.1.

EXAMPLE 36

After 13 1 ml of concentrated hydrochloric acid was added to 500 ml of ethanol, and then 35.0 g of $N^2$-(1-ethoxycarbonyl-3-oxo-3-phenylpropyl)-$N^6$-trifluoroacetyl-L-lysine obtained in Example 35 was dissolved in this solvent, the hydrogenation was carried out at 40° C. under atmospheric pressure by adding 10.5 g of 10% palladium/carbon. After the reaction was over, the catalyst was removed by suction filtration, and the pH of this ethanol solution was adjusted to 4.5 with NaOH. Water was added thereto and ethanol was distilled away by evaporating under reduced pressure, resulting in substitution of ethanol with water.

There was obtained 32.0 g of $N^2$-(1-ethoxycarbonyl-3-phenyl-propyl)-$N^6$-trifluoroacetyl-L-lysine by filtration of the precipitated white crystals. The ratio of the (S,S) form/the (R,S) form was 81.9/18.1. By recrystallizing this product from water-ethanol, $N^2$-(1-(S)-ethoxycarbonyl-3-phenylpropyl)-$N^6$-trifluoroacetyl-L-lysine was obtained.

The obtained product had the following properties.
$^1$H-NMR(90 MHz, CDCl$_3$): & (ppm); 1.2 to 1.43 (t, 3H), 1.42 to 2.25 (m, 8H), 2.5 to 2.85 (m, 2H), 3.0 to 3.55 (m, 4H), 4.05 to 4.35 (q, 2H), 6.9 to 7.4 (m, 5H) IR(cm$^{-1}$, KBr disk): 3320,1740, 1700, 1615, 1205, 1170, 750, 700.
mp: 135.5° to 137.0° C.
$[\alpha]_D^{25} = +7.8°$ (c=2.0, EtOH).

EXAMPLE 37

After 8.16 g of t-EBA was dissolved in 100 ml of ethanol and then 9.69 g of L-Lys (Tfa) was suspended therein, the reaction mixture was cooled to −5° C. And thereto, 20.0 ml of a solution of 1N-LiOH was continuously added dropwise over 150 minutes while stirring the mixture, and the stirring was continued for an additional 30 minutes after the addition was over. The internal temperature of the reaction mixture was kept at −5° C. during the reaction. After the reaction was stopped by adding 10 0 ml of concentrated hydrochloric acid, the hydrogenation was carried out at 40° C. under atmospheric pressure by adding 5.0 g of 10% palladium/carbon.

The catalyst was removed at the end of the reaction, and 14.1 g of $N^2$-(1-ethoxycarbonyl-3-phenylpropyl)-$N^6$-trifluoroacetyl-L-lysine was obtained after treating the mixture in the same manner as in Example 36. The ratio of the (S,S) form/the (R,S) form was 82.0/18.0.

EXAMPLE 38

To 50 ml ethanol were added 4.84 g (20 mmol) of $N^6$-trifluoroacetyl-L-lysine and 4.08 g (20 mmol) of ethyl-β-benzoylacrylate, and the mixture was cooled to each of the temperatures shown in Table A below, while stirring. And thereto was added 20 ml of 1N aqueous solution of lithium hydroxide continuously over 150 minutes. After 30 minutes of reaction, 4.2 ml of concentrated hydrochloric acid was added to stop the reaction, and HPLC analysis was carried out to give the results shown in Table A.

TABLE A

| reaction tempera- ture (°C.) | amount of the (αS,1S)-form (g) | amount of the (αR,1S)-form (g) | (αS,1S)/ (αR,1S) | yield* (%) |
|---|---|---|---|---|
| 0 | 6.65 | 1.56 | 81/19 | 92 |
| −5 | 6.66 | 1.46 | 82/18 | 91 |
| −20 | 6.66 | 1.46 | 82/18 | 91 |
| −30 | 4.91 | 1.15 | 81/19 | 68 |
| −50 | 0 | 0 | — | 0 |

(Note)
*The yield is a total yield of (αS,1S) form and (αR,1S) form.

In addition to the ingredients used in the above Examples, other ingredients can be used in the Examples as set forth in the specification to obtain substantially the same results.

I claim:

1. A process for preparing (αS,1S)-ethyl-α-(1-carboxyethyl)amino-γ-oxo-γ-phenylbutyrate from ethyl-β-benzoylacrylate and (S)-alanine, which comprises forming a lithium salt of (S)-alanine, reacting the obtained salt with at least an equivalent amount of trans-ethyl-β-benzoylacrylate based on the lithium salt in a solvent consisting essentially of ethanol at a temperature ranging from −10° C. to 60° C. to form a Michael addition product, and adding not less than an equivalent amount of acid after completion of the Michael addition to prevent conversion of the (αS,1S)-form of the product into the (αR,1S)-form.

2. The process of claim 1, wherein an acid is added to the reaction system after completion of the addition reaction to neutralize the reaction system, and (αS,1S)-ethyl-α-(1-carboxyethyl)amino-γ-oxo-γ-phenylbutyrate is crystallized.

3. A process for preparing (αS,1S)-ethyl-α-(1-carboxyethyl)amino-γ-oxo-γ-phenylbutyrate from ethyl-β-benzoylacrylate and (S)-alanine, which comprises forming a potassium salt of (S)-alanine, reacting the obtained salt with at least an equivalent amount of cis-ethyl-β-benzoylacrylate based on the potassium salt in a solvent consisting essentially of ethanol at a temperature ranging from −10° C. to 60° C. to form a Michael addition product, and adding not less than an equivalent amount of an acid after completion of the Michael addition to prevent conversion of the (αS,1S)-form of the product into the (αR,1S)-form.

4. The process of claim 3, wherein an acid is added to the reaction system after completion of the addition reaction to neutralize the reaction system, and (αS,1S)-ethyl-α-(1-carboxyethyl)amino-γ-oxo-γ-phenylbutyrate is crystallized.

5. A process for preparing (αS,1S)-ethyl-α-(1-carboxyethyl)amino-γ-phenylbutyrate, which comprises preparing (αS,1S)-ethyl-α-(1-carboxyethyl)amino-γ-oxo-γ-phenylbutyrate by a process comprising forming a lithium salt of (S)-alanine, reacting the obtained salt with at least an equivalent amount of trans-ethyl-β-benzoylacrylate based on the lithium salt in a solvent consisting essentially of ethanol at a temperature ranging from −10° C. to 60° C. to form a Michael addition product, adding not less than an equivalent amount of an acid after the completion of the Michael addition to prevent conversion of the (αS,1S)-form of the product into the (αR,1S)-form, and then catalytically reducing the (αS,1S)-ethyl-α-(1-carboxyethyl)amino-γ-oxo-γ-phenylbutyrate.

6. A process for preparing (αS,1S)-ethyl-α-(1-carboxyethyl)amino-γ-phenylbutyrate, which comprises preparing (αS,1S)-ethyl-α-(1-carboxyethyl)amino-γ-oxo-γ-phenylbutyrate by a process comprising forming a potassium salt of (S)-alanine, reacting the obtained salt with at least an equivalent amount of cis-ethyl-β-benzoylacrylate based on the potassium salt in a solvent consisting essentially of ethanol at a temperature ranging from −10° C. to 60° C. to form a Michael addition product, adding not less than an equivalent amount of an acid after completion of the Michael addition to prevent conversion of the (αS,1S)-form into the (αR,1S)-form, and then catalytically reducing the (αS,1S)-ethyl-α-(1-carboxyethyl)amino-γ-oxo-γ-phenylbutyrate.

7. A process for preparing $N^2$-(1-ethoxycarbonyl-3-oxo-3-phenylpropyl)-$N^6$-trifluoroacetyl-L-lysine from ethyl β-benzoylacrylate and $N^6$-trifluoroacetyl-L-lysine, which comprises forming a lithium, sodium or potassium salt of $N^6$-trifluoroacetyl-L-lysine reaction system in the presence of an alkali metal hydroxide from $N^6$-trifluoroacetyl-L-lysine, reacting the obtained salt with at least an equivalent amount of trans-ethyl-β-benzoylacrylate based on the lithium, sodium or potassium salt in a solvent consisting essentially of ethanol-water or ethanol at a temperature of not more than 10° C. to form a Michael addition product, and adding not less than an equivalent amount of acid after completion of the Michael addition to prevent conversion of the (S,S) form of the product into the (R,S) form.

8. The process of claim 7, wherein said lithium, sodium or potassium salt of $N^6$-trifluoroacetyl-L-lysine is reacted with said trans-ethyl-β-benzoylacrylate at a temperature of −5° C. to 10° C.

9. The process of claim 7, wherein said salt is a lithium salt and said solvent consists essentially of ethanol.

10. The process of claim 7, wherein said salt is formed in situ by adding said base to a mixture of $N^6$-trifluoroacetyl-L-lysine and ethyl β-benzoylacrylate.

11. A process for preparing $N^2$-(1-(S)-ethoxycarbonyl-3-phenylpropyl)-$N^6$-trifluoroacetyl-L-lysine, which comprises preparing $N^2$-(1-ethoxycarbonyl-3-oxo-3-phenylpropyl)-$N^6$-trifluoroacetyl-L-lysine by a process comprising forming a lithium, sodium or potassium salt of $N^6$-trifluoroacetyl-L-lysine in a reaction system in the presence of an alkali metal hydroxide from $N^6$-trifluoroacetyl-L-lysine, reacting the obtained salt with at least an equivalent amount of trans-ethyl-β-benxoylacrylate based on the lithium, sodium or potassium salt in a solvent consisting essentially of ethanol-water or ethanol at a temperature of not more than 10° C. to form a Michael addition product, adding not less than an equivalent amount of acid after the completion of the Michael addition to prevent conversion of the (S,S) form of the product into the (R,S) form, and then catalytically reducing the $N^2$-(1-ethoxycarbonyl-3-oxo-3-phenylpropyl)-$N^6$-trifluoroacetyl-L-lysine.

12. The process of claim 11, wherein said salt is a lithium salt and said solvent consists essentially of ethanol.

13. The process of claim 11, wherein said salt is formed in situ by adding said base to a mixture of $N^6$-trifluoroacetyl-L-lysine and ethylβ-benzoylacrylate.

14. The process of claim 11, wherein said lithium, sodium or potassium salt is reacted with said trans-ethyl-β-benxoylacrylate at a temperature of −5° C. to 10° C.

* * * * *